(12) United States Patent
Murray et al.

(10) Patent No.: US 8,512,770 B2
(45) Date of Patent: Aug. 20, 2013

(54) SKIN PENETRATION COMPOSITION

(75) Inventors: Daniel G. Murray, Ormond Beach, FL (US); Michael W. McDonough, Ormond Beach, FL (US)

(73) Assignee: Dominion Resources Unlimited, LLC, Ormond Beach, FL (US)

( * ) Notice: Subject to any disclaimer, the term of this patent is extended or adjusted under 35 U.S.C. 154(b) by 0 days.

(21) Appl. No.: 13/183,689

(22) Filed: Jul. 15, 2011

(65) Prior Publication Data

US 2012/0034320 A1 Feb. 9, 2012

Related U.S. Application Data

(60) Provisional application No. 61/400,859, filed on Aug. 4, 2010.

(51) Int. Cl.
*A61K 47/00* (2006.01)
*A61K 47/02* (2006.01)
*A61K 47/06* (2006.01)

(52) U.S. Cl.
USPC ........... 424/757; 424/680; 424/725; 424/777; 424/776; 424/679; 424/1.77; 424/767; 424/744; 424/739; 424/400; 514/828; 514/887

(58) Field of Classification Search
None
See application file for complete search history.

(56) References Cited

U.S. PATENT DOCUMENTS

| | | | |
|---|---|---|---|
| 4,278,684 A | 7/1981 | Van Der Veken | |
| 5,006,557 A | 4/1991 | Siu-Ming | |
| 5,037,641 A | 8/1991 | Juhos | |
| 5,487,884 A | 1/1996 | Bissett | |
| 5,849,315 A * | 12/1998 | Rerek et al. | 424/401 |
| 5,879,662 A | 3/1999 | Gieselmann | |
| 6,103,272 A | 8/2000 | Keeney | |
| 6,294,186 B1 * | 9/2001 | Beerse et al. | 424/405 |
| 6,440,437 B1 | 8/2002 | Krzysik | |
| 6,482,442 B1 | 11/2002 | Dado | |
| 6,544,534 B2 | 4/2003 | Malmgren | |
| 6,579,543 B1 | 6/2003 | McClung | |
| 6,921,529 B2 | 7/2005 | Maley | |
| 7,303,768 B2 | 12/2007 | Yoo | |
| 2003/0039668 A1 | 2/2003 | Gulla | |
| 2004/0106163 A1 | 6/2004 | Workman | |
| 2004/0202726 A1 | 10/2004 | DeShay | |
| 2005/0048130 A1 | 3/2005 | Marchioni | |
| 2008/0193393 A1 | 8/2008 | Dayan | |
| 2008/0286390 A1 | 11/2008 | Tanyi | |
| 2009/0068255 A1 * | 3/2009 | Yu et al. | 424/450 |
| 2009/0162304 A1 | 6/2009 | Dileva | |
| 2009/0258098 A1 | 10/2009 | Rolling | |
| 2009/0281197 A1 | 11/2009 | Kinsinger | |
| 2010/0076035 A1 | 3/2010 | Carter | |
| 2010/0173007 A1 | 7/2010 | Dileva | |

OTHER PUBLICATIONS

Selvam et al. (Transdermal drug delivery systems for antihypertensive drugs—A review, Feb. 24, 2010, International Journal of Pharmaceutical and Biomedical Research, vol. 1, pp. 1-8).*
Davis et al (Cosmeceuticals and natural products: wound healing, Sep.-Oct. 2009, Clinics in Dermatology, vol. 27, pp. 502-506).*

* cited by examiner

*Primary Examiner* — Cherie M Stanfield
*Assistant Examiner* — Mark V Stevens
(74) *Attorney, Agent, or Firm* — Brian S. Steinberger; Joyce Morlin; Law Offices of Brian S. Steinberger, P.A.

(57) ABSTRACT

The present invention comprises an all-natural composition of matter and methods of delivering nutrients, medicines, pain relievers, antioxidants, antidotes, antibiotics and various active ingredients and supplements directly to the affected area of the body. The all-natural carrier composition consists essentially of the combination of a natural oil, water, salt(s), natural emulsifier, natural sugar(s), plant extracts, natural acid(s), starch and natural flavor(s). The active substances that are mixed with the all-natural carrier composition, include, but are not limited to, drugs, vitamins, minerals, antibiotics anti-fungal agents, antioxidants, diuretics, allergy medicines, anti-inflammatory agents, muscle relaxers, pain reducers, diabetic drugs, neuropathy drugs, chemotherapy agents, arthritis drugs, lotions for eczema, shingles, psoriasis, skin rash; herbal medicines, erectile dysfunction drugs, hormones, cholesterol drugs, essential fatty acids, and the like. The all-natural carrier composition facilitates the penetration of active substances into the dermal layer of the skin.

7 Claims, No Drawings

SKIN PENETRATION COMPOSITION

The present application claims the benefit of priority from U.S. Provisional Patent Application Ser. No. 61/400,859 filed on Aug. 4, 2010, which is incorporated herein by reference.

FIELD OF THE INVENTION

The present invention relates generally to skin penetration compositions, and more specifically to, a topically applied, dermal layer penetrating composition that delivers natural supplements and active therapeutic substances to areas of the body requiring treatment.

BACKGROUND AND PRIOR ART

Many medications and prescription drugs are taken orally or via injection; as a result, chemicals are necessarily distributed throughout the whole body of humans and other mammals, potentially causing various harmful side effects. Some of the side effects associated with prescription drugs and other over-the-counter medications that are distributed throughout the whole body, include, but are not limited to, stomach upset, liver toxicity, irritability, gastric problems, confusion, high or low blood pressure, nervousness, dizziness, crying, fainting, restlessness, irregular heart rate, cataracts, blurred vision, shortness of breath, loss of bowel control, seizures and tremors, mental depression, aggression and even premature death of the mammal.

The harmful side effects create a long-felt and unfilled need to deliver therapeutic medication and natural ingredients only to the affected area of the body so that mammals do not suffer the terrible side-effects of the medication.

Various patents provide the state of the art in topical skin formulations that include chemical and natural ingredients. A representative example of patents and patent publications is provided below.

US Patent Publication 2010/0173007 to DiLeva teaches a topical composition for treating skin diseases which include rashes, blisters, acne, fungal infections, bacterial infections, bums, insect bites, microbial infections, sunburn, scabies, scrapes, cuts and combinations thereof.

US Patent Publication 2010/0076035 to Carter discloses a topical formulation for delivery of bioactive substances to skin, fingernails, toenails, ocular tissue, vagina, rectum (as a suppository), and other tissue surfaces containing an epithelial cell layer, formulation includes a vasoactive agent, an osmolyte, and an active ingredient including penetration enhancers.

US Patent Publication 2009/0281197 to Kinsinger et al. discloses a skin penetrating gel combined with acetic acid (another name for vinegar) and thymol for treating the toe or finger nail.

US Patent Publication 2009/0258098 to Rolling et al. discloses an antifungal composition that includes various fungistatic and fungicidal essential oil components, or combinations thereof. The penetrating carrier system may include various ingredients, including a penetration enhancer, such as isopropyl myristate.

US Patent Publication 2009/0162304 to DiLeva claims a topical composition treating skin diseases; may include vitamins and medicaments.

US Patent Publication 2008/0286390 to Tanyi discloses a skin care composition contains plurality of essential fatty acids derived from natural oils, which include both botanicals and oils derived from animal sources for surface skin care.

US Patent Publication 2008/0193393 to Dayan teaches controlled release and targeted delivery of topically applied compounds, such as fragrances, pigments, skin treatment agents, topical drugs, and similar topically applied compounds to the surface of the skin.

US Patent Publication 2005/0048130 to Marchioni teaches colloidal silver is an effective natural antibiotic. US Patent Publication 2004/0202726 to DeShay discloses a topical composition useful for reducing blood pressure having a liquid carrier containing, water, potassium chloride, and a penetrant enhancer for enhancing the penetration of the potassium chloride into the skin; uses olive oil and aloe vera.

US Patent Publication 2004/0106163 to Workman et al. discloses delivery of SMMR's (small molecule metabolite reporters) that indicate rate of glycolysis within the living cell loci; materials listed aid the process of skin penetration for SMMRs and create a diffusion rate enhancing solvent system for transdermal delivery: acetic acid or soybean oil, hazelnut oil, jojoba oil, sweet almond oil, olive oil, calendula oil, apricot kernel oil, grapeseed oil, wheat germ oil, and emu oil. US Patent Publication 2003/0039668 to Gulla teaches combination of lecithin, or the phosphatides within lecithin, or a saponoside; combined with one or more surfactants, preferably one or more essential oils, one or more gel formers, and water, all in controlled concentration, can be combined to form a high water content emulsion that is capable of rapid penetration into the epidermis.

U.S. Pat. No. 7,303,768 to Yoo discloses topically applied drugs including bile salts, glucose, guar gum or pectin.

U.S. Pat. No. 6,921,529 to Maley teaches vinegar as a skin penetrant for feet fungus.

U.S. Pat. No. 6,579,543 to McClung discloses a topical application may comprise aloe vera, oils, such as, omega-3 and omega-6, linoleic; licorice as an anti-inflammatory.

U.S. Pat. No. 6,544,534 to Malmgren discloses a skin conditioner and soap made of sea salt, Epsom salt, almond oil, apricot kernel oil, avocado oil, jojoba oil, aloe vera gel, castor oil, vitamin E, vegetable glycerin.

U.S. Pat. No. 6,482,442 to Dado discloses the topical use of a substance mixture comprising honey and olive oil.

U.S. Pat. No. 6,440,437 to Krzysik discloses an oil-in-water wipe that includes aloe vera or honey or glucose humectants; oils and fats.

U.S. Pat. No. 6,103,272 to Keeney discloses a method that includes applying a topical solution containing colloidal silver to the scalp, may include distilled water, sea salt, aloe vera, vitamins, iodine, ginseng, and/or vinegar; may include vitamins E, A, and can convert the topical solution to be orally administered.

U.S. Pat. No. 5,879,662 to Bissett teaches: xanthan gum and agar-agar as natural thickening agents; may use vinegar, may include lecithin, may use licorice for a different purpose as a soothing agent, may include flavoring agents, for example, peppermint oil.

U.S. Pat. No. 5,487,884 to Bissett cited to show that aloe vera is a natural anti-inflammatory agent.

U.S. Pat. No. 5,037,641 to Juhos teaches cholesterol as art-recognized natural emulsifier (surfactant).

U.S. Pat. No. 5,006,557 to Herstein teaches acetic acid is able to penetrate into skin dermis and is useful in acne compositions.

U.S. Pat. No. 4,278,684 to Van derVeken et al. teach a non-toxic drug composition with substituted acetic acid as skin penetration promoter.

Thus, the prior art suggests that many chemical and natural compounds have at some time been used in topical skin compositions as a medicament. What is absent in the prior art is the formulation of a universal, i.e., capable of delivering water soluble and fat soluble active substances, all-natural, skin penetrating carrier composition that delivers active therapeutic substances to the dermal layer of the skin in the area of the body requiring treatment. The present invention fulfills this need.

SUMMARY OF THE INVENTION

The first objective of the present invention is to provide a composition of all-natural ingredients formulated to carry and facilitate the penetration of active ingredients into the dermal layer of the skin.

The second objective of the present invention is to provide a composition of all-natural ingredients that functions as a carrier to deliver active components to an affected area of the body and affect only the area to which it is applied. The third objective of the present invention is to provide a composition of all-natural ingredients that functions as a carrier of active ingredients, including, but not limited to, drugs, vitamins, minerals, antibiotics, anti-fungal agents, antioxidants, diuretics, allergy medicines, anti-inflammatory agents, muscle relaxers, pain reducers, diabetic drugs, neuropathy drugs, chemotherapy agents, arthritis drugs, lotions for eczema, shingles, psoriasis, skin rash; herbal medicines, erectile dysfunction drugs, hormones, cholesterol drugs, essential fatty acids, and the like.

The fourth objective of the present invention is to provide a composition of all-natural ingredients that functions as a carrier with ingredients selected from the following skin-penetrating components: water. Oleo Eurpoaea (olive oil), acetic acid, lecithin, honey, aloe vera, salt, starch, and natural flavors.

The fifth objective of the present invention is to provide a composition of all-natural ingredients that functions as a carrier of active ingredients to deep tissue and nerve endings in the inner dermal layers of the skin resulting in decreased nerve pain, muscle pain, improvement of carpal tunnel syndrome, decreasing the nerve pain of shingles, fibromyalgia, leg pain from spinal stenosis and pain of reflex sympathetic dystrophy.

The sixth objective of the present invention is to provide a composition of all-natural ingredients that functions as a carrier of both water and fat soluble active substances into the inner skin layers.

The seventh objective of the present invention is to provide a composition of all-natural ingredients that functions as a carrier of active substances or natural supplements and antioxidants into dermal or inner layers of the skin, thus preventing the systemic side effects encountered by orally administered medication or over-the-counter drugs.

The eighth objective of the present invention is to provide a composition of all natural ingredients that functions as a carrier of active substances, natural supplements and antioxidants in effective doses that are lower than doses required by oral administration because the medication is delivered to the affected area of the body, such as an infection site, the genital area, area of localized pain, and to cancerous tissue.

Further objects and advantages of this invention will be apparent from the following detailed description of a presently preferred embodiment, when read in conjunction with the appended claims.

DETAILED DESCRIPTION OF THE PREFERRED EMBODIMENT

Before explaining the disclosed embodiment of the present invention in detail, it is to be understood that the invention is not limited in its application to the details of the particular arrangement shown since the invention is capable of other embodiments. Also, to the terminology used herein is for the purpose of description and not of limitation.

It would be useful to discuss the meanings of some words used herein and their applications before discussing the compositions of matter and method of using as a carrier in a topical skin application.

The term, "carrier" is used herein to mean a composition of natural ingredients formulated to function as the medium by which active substances are conveyed to the skin of an affected part of the body.

The phrase, "composition of matter" is used herein to mean a combination of natural ingredients to form a lotion, gel, cream, paste, foam, aerosol spray, and the like.

The term, "topical" is used herein to mean the application of a substance to a specific area of the skin.

The term, "universal" is used herein to mean adapted or adjustable to meet varied requirements for effective delivery of either water soluble or fat soluble active substances.

The composition of matter of the present invention is to be marketed under the trade name RELIEVZ™, a tradename owned by Dominion Resources Unlimited, LLC, a Florida Corporation, 58 Mayfield Terrace, Ormond Beach, Fla., the same owner as that of the subject patent application.

The present invention comprises a natural composition of matter and a method of delivering nutrients, medicines, pain relievers, antioxidants, antidotes, antibiotics and various active ingredients and natural supplements directly to the affected area of the body.

The composition of matter of the present invention is composed of all natural materials and does not require the use of any chemicals to help the medicinal or nutritive compounds to be absorbed by the skin. This is an advantage over the prior art wherein chemicals are used, sometimes at very high levels, to increase absorption. The use of chemicals can cause harmful side effects.

The present invention is a composition of natural ingredients and a method for topically applying the formula to deliver various active ingredients through the skin. The basic, all-natural carrier composition consists of a natural oil, water, salt(s), natural emulsifier, natural sugar(s), plant extracts, natural acid(s), starch and other thickeners or hydrocolloids and natural flavor(s).

Examples of natural oils that are used in the composition of the present invention include, and are not limited to, almond oil, apricot kernel oil, avocado oil, grape seed oil, jojoba oil, kukui nut oil, fractionated coconut oil, olive oil, sesame oil, sunflower oil, wheat germ oil, canola oil corn oil, cottonseed oil, safflower oil and mixtures thereof.

Water suitable for the present invention is potable water that can be deionized. filtered, distilled, or tap water from the spigot.

Salts useful in the present invention function as osmolytes and may be selected from chlorides of sodium, potassium, ammonium, calcium and sea salt.

Natural emulsifiers are used to keep the water and oil in the formulation from separating. Suitable emulsifiers for the present invention, include, and are not limited to, soy lecithin, guar gum, fruit pectin, including apple pectin, grapefruit pectin, orange pectin and the like.

Natural sugars are used to increase water activity and enhance skin penetration. Sugars are selected from honey, cane sugar, beet sugar, corn syrup, molasses, natural sugars, turbinado sugar and mixtures thereof.

Plant extracts from succulent plants varieties are used to enhance skin penetration include, and are not limited to, aloe vera, cacti and seaweed extract.

Natural acids are used as preservatives and to enhance skin penetration and are selected from acids such as acetic acid (vinegar), lactic acid, malic acid, phosphoric acid, ascorbic acid, glycolic acid and salicylic acid.

Starch used in the present invention is selected from the group consisting of corn starch, wheat starch, tapioca starch, waxy maize starch, rice starch, high amylose starch and potato starch. Other hydrocolloids such as guar gum, gum tragacanth, gum Arabic and gums, such as Xanthan gum, produced by fermentation could be used as thickeners.

Natural flavors are used to provide a pleasant aroma and, include, but are not limited to, cinnamon, vanilla, coriander, citrus, peppermint and the like.

It is known that the skin is a soft outer covering of a mammal and is made up of multiple layers of ectodermal tissue that guards the underlying muscles, bones, ligaments and internal organs. The outermost layer of the skin provides an outstanding barrier against the external environment, protecting the body against pathogens and excessive water loss. Mammalian skin is composed of two primary layers, the epidermis and the dermis. The epidermis is the outermost layer which provides waterproofing and serves as a barrier to infection. The epidermis is also responsible for skin impermeability toward most solutes.

The dermis, or dermal layer, serves as a location for the appendages of skin and to is the layer of skin beneath the epidermis. The dermis harbors the nerve endings that provide the sense of touch and heat.

It should be noted that the hypodermis is not part of the skin, and lies below the dermis. The hypodermis attaches the skin to underlying bone and muscle as well as supplies the dermis with blood vessels and nerves. Another name for the hypodermis is the subcutaneous tissue.

The all-natural skin penetration composition of the present invention delivers both fat soluble and water soluble active ingredients through the epidermal and dermal layers of skin where nerve endings are located.

The all-natural composition of the present invention delivers active components to an affected area of the body. The body can be any mammal, such as, but not limited to a human, pig, rat, cow, sheep; the preferred mammal is a human. The active substances could be any of a number of active ingredients, including, but not limited to, drugs, vitamins, minerals, antibiotics, anti-fungal, antioxidants, diuretics, allergy medicines, anti-inflammatory, muscle relaxers, pain reducers, lotions for eczema; shingles, psoriasis, skin rash, herbal medicines, erectile dysfunction drugs, hormones, cholesterol drugs, essential fatty acids, and the like.

One example is the use of the all-natural skin penetration carrier composition to deliver chemotherapy products directly to the affected area of the body to help avoid the terrible side effects on the rest of the body. Chemotherapy drugs cause such devastating side effects as nausea, hair loss, weakness, loss of appetite, diarrhea and the like.

Another example would be using the composition of the present invention to deliver an erectile dysfunction medicine directly to the genital area to avoid high blood pressure problems for those with heart conditions. The all-natural composition is also particularly useful for delivering anti-viral compounds to help relieve symptoms of shingles and herpes and to deliver anti-cancer compounds for skin cancers.

In addition, there are a number of diseases that cause loss of feeling and sensory deprivation. Diseases like diabetes cause pain, numbness and weakness in the outer extremities (feet and hands, etc.). This natural delivery system can help deliver healing nutrients, pain relievers and medicines without directly affecting the stomach and other areas of the body when these active ingredients are taken orally.

The composition of the present invention provides a combination of all-natural ingredients formulated into various topical applications. The topical application can be in the form of a lotion, cream, gel, paste, foam, aerosol spray that is applied to an affected area of the body. The composition of the present invention can also be modified for oral administration.

The method for using the all-natural topically applied composition is to add a powdered or liquid form of an active substance or natural supplement to the composition of the present invention, if necessary, remove hair from the epidermis in the affected area of the body, apply the mixture to the epidermis layer of the skin and rub it in. This topically applied formula penetrates through the epidermis to the dermis layer of the skin to deliver an active substance directly to the affected area.

Table I below provides a list of ingredients that are used to provide a basic skin penetrating carrier composition used to prepare 100 weight percent of the formulation, which is subsequently mixed with an active substance in a range of from approximately 0.20 weight percent to approximately 7.0 weight percent of the total formulation. A person skilled in the art is knowledgeable as to the exact quantities of thickener (viscosity agent) and aromatic essence that produce the desired topical skin lotion that is commercially marketable and acceptable. A person skilled in the art is also knowledgeable as to the exact quantities of active substances to add based on the diagnosis and treatment required by a patient.

TABLE I

Basic Skin Penetration Carrier Composition

| Ingredient | Function |
|---|---|
| Water | Aqueous phase, skin penetrating |
| *Oleo Europaea* (Olive) Fruit Oil | Emollient |
| Acetic Acid | Preservative, skin penetrating |
| Soy Lecithin | Emulsifier |
| Honey | Water activity, skin penetrating |
| *Aloe Vera* | Skin penetrating |
| Salt | Osmolarity, skin penetrating |
| Starch | Viscosity agent |
| Cinnamon | Aroma |

In Table II below the formulation of the skin penetrating lotion is provided with a preferred target weight percent of each component.

TABLE II

Weight Percent of Ingredients

| Ingredient | Preferred Wt. % | Most Preferred Wt. % |
|---|---|---|
| Water | 46-65 | 48-60 |
| *Oleo Europaea* (Olive) Fruit Oil | 12-25 | 17-23 |
| Acetic Acid | 5.0-8.0 | 6.0-7.5 |
| Soy Lecithin | 3.5-6.0 | 4.0-6.0 |
| Honey | 2.5-5.5 | 3.5-5.5 |
| *Aloe Vera* | 1.5-3.5 | 2.5-3.0 |
| Salt | 2.0-3.1 | 2.4-3.0 |
| Starch | 2.5-4.0 | 3.0-3.5 |
| Cinnamon | 0.8-1.3 | 0.9-1.2 |

In actual trials, subjects were administered the topically applied composition of the present invention to alleviate pain and improve the sensation of feel in various parts of the body. It was completely unexpected that natural ingredients can penetrate through the epidermal and dermal layers of the skin to a depth that delivers active ingredients directly to the affected part of the body.

In the examples below, natural supplements or active substances were mixed with a selected carrier composition from Table II above. The active substances include B vitamins and a natural antioxidant that are added to the carrier solution and thoroughly blended.

The natural antioxidant is selected from at least one of grape seed extract, selenium, alpha lipoic acid, extracts of fruits such as cranberry, blueberry, blackberry, prune, cherry, and a mixture thereof. The B vitamins include at least one of the eight B vitamins, Vitamin B1 (Thiamine), Vitamin B2 (Riboflavin) Vitamin B3, also Vitamin P or Vitamin PP (Niacin), Vitamin B4 (Adenine), Vitamin B5 (Pantothenic acid), Vitamin B6 (Pyridoxine), Vitamin B7, also Vitamin H (Biotin), Vitamin B9, also Vitamin M and Vitamin B-c (Folic acid), Vitamin 1112 (Cobalamin) and mixtures thereof. The amount and composition of the active substances mixed with the carrier composition varies within a range of 93.0 wt % to 98 wt % carrier composition of the present invention and 1.25 wt % to 7.00 wt % active substance. The active substance for the examples below consists of 0.01 wt % to 0.25 wt % B vitamins mixed with 1.1 wt % to 2.4 wt % natural antioxidant.

Thus, someone skilled in the art makes a judicious selection of carrier composition and active ingredient composition as required; selection is dependent on the to condition to be treated and is not a limitation of the present invention. The combined mixture of carrier composition and active substance is identified as the Relievz™ lotion in the examples below.

EXAMPLE 1

Physician Observation re: Fibromvalgia and Shingles

A 59 year old female, Patient A, who was initially diagnosed with fibromyalgia and was on prescription drugs, Cymbalta® (duloxetine HCl) and pregabalin (400 mg, daily) with no relief. The patient has also used topical Biofreeze® pain reliever, Voltaren (diclofenac sodium) gel, and Cryoderm™ pain relief, with no improvement. Patient A used the composition of the present invention, Relievz™ lotion twice daily to the affected areas and experienced considerable relief. The patient subsequently contracted herpes zoster (shingles) and applied the Relievz™ lotion twice daily, once the lesions had dried, Patient A experienced immediate relief.

EXAMPLE 2

Physician Observation re: Sciatica and Neuropathy

A 73 year old female, Patient B, with a history of sciatica and neuropathy, eventually diagnosed as diabetic neuropathy was taking gabapentin and subsequently pregabapentin and had continued pain. Patient B applied Relievz™ lotion to the affected areas and stated that she had "considerable improvement and less pain" and ambulation. The patient continues to use Relievz™ lotion daily.

EXAMPLE 3

Physician Observation re: Diabetic Neuropathy and Spinal Stenosis

An 82 year old male, Patient C, who had long term pain with diabetic neuropathy and leg pain from spinal stenosis also suffered from the symptoms of restless leg syndrome. Patient C had received treatment including chiropractic care, physical therapy and gabapentin. The patient's chief complaint was an inability to sleep due to shooting pains into the legs during the night. After using Relievz™ lotion, the patient stated his pain was "almost totally eliminated" and continues to use the Relievz™ lotion to keep the pain under control.

EXAMPLE 4

Physician Observation re: Severe Pain in Foot

A 57 year old male, Patient D, was seen for a four-month complaint of severe pain in his left foot. Difficulty with shoe wear and walking was also reported. Patient D had experienced a laceration injury to his foot with resultant infection. Following the clearance of infection, he had continued pain and disability. The pain involved the areas of the subcutaneous dorsal nerves of the foot, along with the deep peroneal nerve. The patient's diagnosis was reflex sympathetic dystrophy—regional pain syndrome. The patient started the Relievz™ lotion and state the "excruciating pain was reduced immediately" and after three weeks, it was "almost gone." The patient has returned to normal activity.

EXAMPLE 5

Physician Observation re: Shingles Pain

An 83 year old female, Patient E, with a six month history of post herpetic neuralgia (shingles pain) of her lower abdomen, in spite of multiple medications. Patient E applied the Relievz™ lotion twice daily and stated that she was experiencing ". . . additional relief of pain."

Prior to the present invention, it was not known that an all-natural skin penetration carrier composition could deliver active substances into the dermal layer of the skin. This prevents the systemic side effects encountered with orally administered or injected drugs and medications. The targeted delivery of medication to the affected area of the body also allows the administration of lower doses of a supplement, drug or antibiotic.

While the invention has been described, disclosed, illustrated and shown in various terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

We claim:

1. A skin penetration composition which includes a natural carrier composition for delivering active substances to an affected area of a body of a living mammal comprising in combination:

a natural carrier composition that includes:
approximately 46.00% to approximately 65.00% by weight amount of water selected from the group consisting of purified water, deionized water, filtered water and potable water and mixtures thereof;
approximately 12.00% to approximately 25.00% by weight of a natural oil selected from the group consisting of fruit oil, olive oil and mixtures thereof, or approximately 17.00% to approximately 23.00% by weight of natural oil selected from the group consisting of fruit oil, olive oil and mixtures thereof, or an effective amount of natural oil selected from the group consisting of almond oil, apricot kernel oil, avocado oil, grapeseed oil, jojoba oil, kukui nut oil, fractionated coconut oil, olive oil, sesame oil, sunflower oil, wheat germ oil, canola oil, corn oil, cottonseed oil, safflower oil and mixtures thereof;

approximately 2.00% to approximately 3.10% by weight of sodium chloride, or approximately 2.40% to approximately 3.00% by weight of sodium chloride, or an effective amount of a natural salt selected from the group consisting of potassium chloride, ammonium chloride, calcium chloride, sea salt and mixtures thereof;

approximately 3.50% to approximately 6.00% by weight of lecithin, or approximately 4.00% to approximately 6.00% by weight of lecithin, or approximately 3.50% to approximately 5.50% by weight of soy lecithin, or an effective amount of a natural emulsifier selected from the group consisting of guar gum and fruit pectin;

approximately 2.50% to approximately 5.50% by weight of honey, or an effective amount of a natural sugar selected from the group consisting of cane sugar, beet sugar, corn syrup, molasses, turbinado sugar and mixtures thereof;

approximately 1.50% to approximately 3.50% by weight of aloe vera(dry), or approximately 1.50% to approximately 3.50% aloe vera(dry), or approximately 1.50% to approximately 3.50% by weight of aloe vera, or an effective amount of a plant extract selected from the group consisting of aloe vera, seaweed, and cacti;

approximately 5.00% to approximately 8.00% by weight of acetic acid, or approximately 6.00% to approximately 7.50% by weight of acetic acid, or an effective amount of a natural acid selected from the group consisting of lactic acid, malic acid, phosphoric acid ascorbic acid, glycolic acid and salicylic acid; and approximately 2.50% to approximately 4.00% by weight of corn starch, or approximately 3.00% to approximately 3.50% by weight of corn starch, or an effective amount of a natural starch selected from the group consisting of corn starch, wheat starch, tapioca starch, waxy maize starch, rice starch, amylose starch and potato starch wherein the topical application to the skin of an animal enhances skin penetration of active substances to a dermal layer; and an active substance mixed with the natural carrier composition, wherein the natural carrier composition delivers the active substance to the affected area of the body.

2. The skin penetration composition of claim 1, wherein the carrier composition comprises,
(a) approximately 46.00% to approximately 65.00% by weight of water;
(b) approximately 12.00% to approximately 25.00% by weight of olive oil;
(c) approximately 1.50% to approximately 3.50% by weight of aloe vera (dry);
(d) approximately 2.50% to approximately 5.50% by weight of honey;
(e) approximately 3.50% to approximately 6.00% by weight of lecithin;
(f) approximately 2.00% to approximately 3.10% by weight of sodium chloride;
(g) approximately 5.00% to approximately 8.00% by weight of acetic acid; and
(h) approximately 2.50% to approximately 4.00% by weight of corn starch,
wherein the skin penetration composition is a carrier for active substances to treat an affected area of an animal requiring treatment.

3. The skin penetration composition of claim 1, wherein the carrier compostion further includes:
an effective amount of a natural flavor to provide a pleasant aroma, wherein the natural flavor is selected from the group consisting of cinnamon, cinnamon oil, vanilla, coriander, peppermint and citrus.

4. The skin penetration composition of claim 3 wherein the natural flavor is at least one of cinnamon and cinnamon oil used in an amount that is approximately 0.80% to approximately 1.30% by weight of the total formulation.

5. The skin penetration composition of claim 2, wherein the carrier composition comprises,
(a) approximately 48.00% to approximately 60.00% by weight of water;
(b) approximately 17.00% to approximately 23.00% by weight of olive oil;
(c) approximately 2.50% to approximately 3.00% by weight of aloe vera (dry);
(d) approximately 3.50% to approximately 5.50% by weight of honey;
(e) approximately 4.00% to approximately 6.00% by weight of lecithin;
(f) approximately 2.40% to approximately 3.00% by weight of sodium chloride;
(g) approximately 6.00% to approximately 7.50% by weight of acetic acid; and
(h) approximately 3.00% to approximately 3.50% by weight of corn starch,
wherein the skin penetration composition is a carrier for active substances to treat an affected area of an animal requiring treatment.

6. The skin penetration composition of claim 5, wherein the carrier composition further includes an effective amount of a natural flavor to provide a pleasant aroma, wherein the natural flavor is at least one of cinnamon and cinnamon oil used in an amount that is approximately 0.90% to approximately 1.20% by weight of the total formulation.

7. The skin penetration composition of claim 5, wherein the natural carrier composition comprises approximately 93.00% to approximately 98.00% by weight of the skin penetration composition; and
wherein the active substance comprises approximately 1.25% to approximately 7.00% by weight of the skin penetration composition.

* * * * *